United States Patent [19]

Inaba et al.

[11] Patent Number: 5,098,607
[45] Date of Patent: Mar. 24, 1992

[54] PROCESS FOR STABILIZING PERCARBOXYLIC ACID

[75] Inventors: Yukio Inaba; Takafumi Hirakawa; Hiromi Yabuta; Hiroyuki Iida, all of Ube, Japan

[73] Assignee: Ube Industries Ltd., Yamaguchi, Japan

[21] Appl. No.: 619,767

[22] Filed: Nov. 29, 1990

[30] Foreign Application Priority Data

Dec. 8, 1989 [JP] Japan ................... 1-317702

[51] Int. Cl.⁵ .............................. C09K 15/18
[52] U.S. Cl. ...................... 252/384; 252/405; 252/407; 562/3
[58] Field of Search ............ 562/3; 252/384, 405, 252/407

[56] References Cited

U.S. PATENT DOCUMENTS

| | | | |
|---|---|---|---|
| 2,609,391 | 9/1952 | Greenspan | 562/3 |
| 3,053,633 | 9/1962 | Dunlop | 562/3 |
| 3,192,254 | 6/1965 | Hayes | 562/3 |
| 3,192,255 | 6/1965 | Cann et al. | 562/3 |
| 4,959,497 | 9/1990 | Dankowski | 562/3 |

FOREIGN PATENT DOCUMENTS 158935 9/1952 Australia .
678212 1/1964 Canada .

Primary Examiner—Deborah L. Kyle
Assistant Examiner—Valerie Fee
Attorney, Agent, or Firm—Frishauf, Holtz, Goodman & Woodward

[57] ABSTRACT

Disclosed is a process for stabilizing a percarboxylic acid characterized in that the percarboxylic acid is mixed with at least one pyridine derivative selected from the group consisting of picoline, ethylpyridine, conyrine, lutidine and N-oxide thereof.

15 Claims, 1 Drawing Sheet

PROCESS FOR STABILIZING PERCARBOXYLIC ACID

BACKGROUND OF THE INVENTION

This invention relates to a process for stabilizing an organic peracid such as a percarboxylic acid, more specifically to a process for stabilizing a solution of a percarboxylic acid such as perpropionic acid, which is used for the reaction with cyclohexanone in the preparation of $\epsilon$-caprolactone.

Among organic peracids which are typical peroxides, particularly a percarboxylic acid is an industrially important material, and is used for various chemical reactions such as epoxidation, hydroxylation, lactonization, formation of quinone, aromatic ring opening, formation of phenol and oxidation of ketone. However, the percarboxylic acid is an inherently unstable material. The percarboxylic acid is decomposed with violence while releasing oxygen due to elevated temperatures or contamination with impurities, whereby danger is incurred in some cases. Further, when left to stand, the percarboxylic acid is liable to be decomposed gradually while releasing oxygen even at room temperature. Thus, the instability is a serious drawback in using the percarboxylic acid.

When the percarboxylic acid exists in a pure state or coexists only with an inert substance, there is no stabilizer which enhances stability in that state. However, in a solution of the percarboxylic acid, particularly in an aqueous solution thereof, a trace amount of a metal ion is generally included, and the decomposition of the percarboxylic acid is accelerated by function of the metal ion as a decomposing catalyst. Therefore, as a stabilizer of the percarboxylic acid which can decrease the function of the metal ion as a decomposing catalyst existing in a solution of the percarboxylic acid, various stabilizers of the percarboxylic acid such as sequestering agents have been investigated.

More specifically, as the stabilizer as described above, there have been proposed stabilizers such as a polyphosphate (e.g. sodium pyrophosphate or sodium tripolyphosphate), ethylenediaminetetraacetic acid, diethylenetriaminepentaacetic acid, potassium thiocyanate, polyaminocarboxylic acid, a picolinic acid, a quinoline derivative, a dipicolinic acid (e.g. pyridine-2,6-dicarboxylic acid), pyridine-2,6-dimethanol, tributyl phosphate and alkyl pyrophosphate and they have been used singly or in combination thereof (see, for example, "Chemical Industry", Vol. 21, August, 1970 and "Special Editing, Organic Peracids and Peroxides—Utilization, Properties and Handling of Peracids" written by Katsutaro Yoshimatsu). Particularly, among these stabilizers, a phosphate such as tributyl phosphate, and a dipicolinic acid are effective, and it has been known that a dipicolinic acid is effective for a solution of the percarboxylic acid with a concentration of 10% by weight or more, but it can not necessarily be said to be satisfactory in the points of its effect and economy.

SUMMARY OF THE INVENTION

An object of the present invention is to provide a process for stabilizing a percarboxylic acid, which can be applied industrially, by using a novel stabilizer in which the above-mentioned problems possessed by the conventionally known stabilizers of the percarboxylic acid have been solved.

The present inventors have investigated intensively to develop a stabilizer which is more excellent in effect than the above-mentioned conventionally known stabilizers, inexpensive and commercially available, and consequently succeeded in finding a novel stabilizer, to accomplish the present invention.

That is, the present invention relates to a process for stabilizing a percarboxylic acid which comprises mixing the percarboxylic acid with at least one pyridine derivative selected from the group consisting of picoline, ethylpyridine, conyrine, lutidine and N-oxide thereof.

DESCRIPTION OF THE PREFERRED EMBODIMENTS

Figure 1:
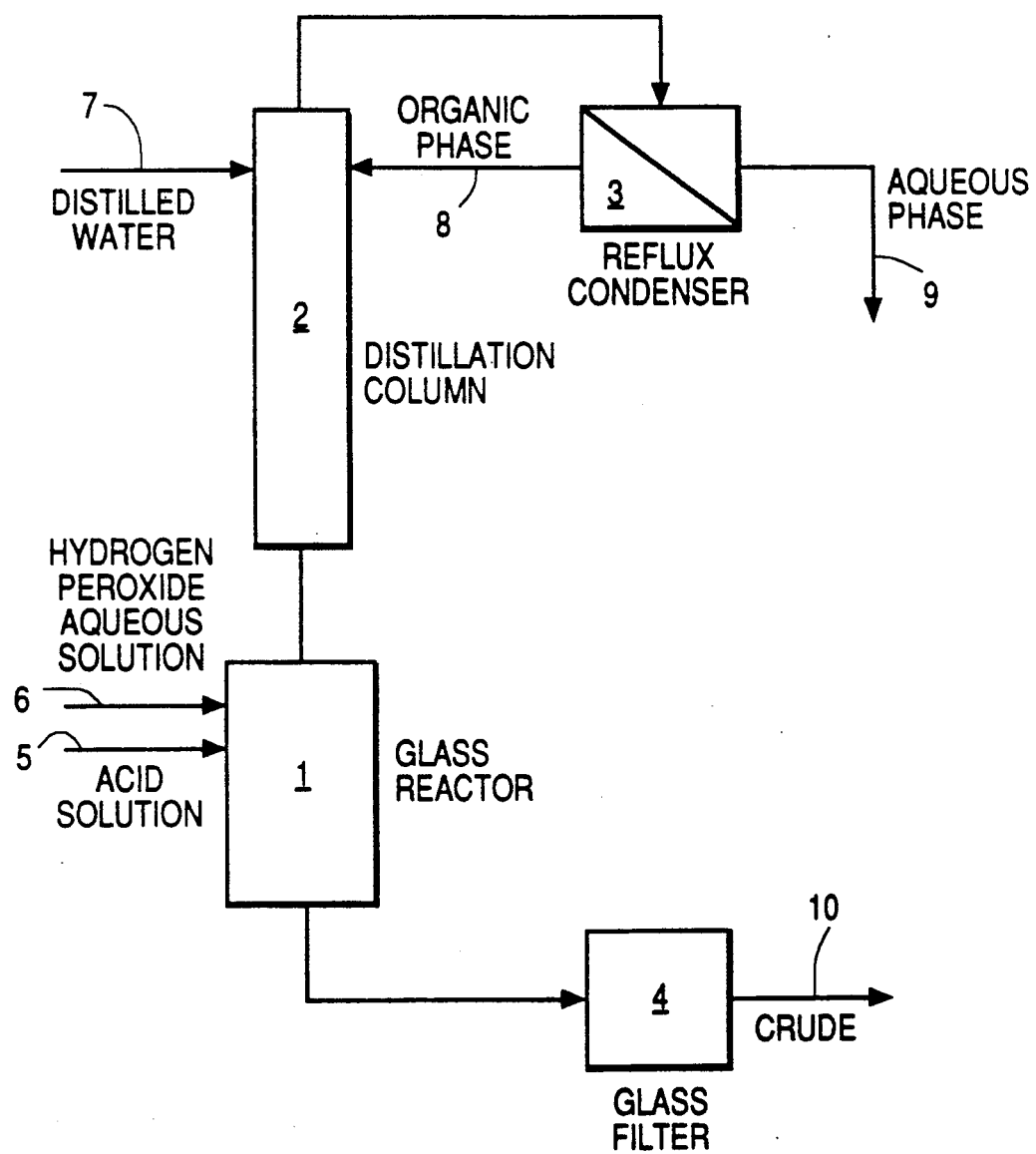
FIGURE 1 is a flow chart showing a summarized operating flow of an experimental apparatus for preparing a perpropionic acid used in Examples 1 to 4 and Comparative examples 1 to 4.

As an organic peracid, particularly a percarboxylic acid which is an object of the process according to the present invention, there may be included, for example, saturated aliphatic monopercarboxylic acids having 1 to 7 carbon atoms such as a performic acid, a peracetic acid, a perpropionic acid, a perbutyric acid, a perisobutyric acid and a perheptoic acid, unsaturated aliphatic monopercarboxylic acids having 3 to 4 carbon atoms such as a percrotonic acid, a perisocrotonic acid, a peracrylic acid and a permethacrylic acid, alicyclic monopercarboxylic acids such as a percyclohexanoic acid and aromatic monopercarboxylic acids such as a perbenzoic acid, a pertoluic acid, a monoperphthalic acid and a per-m-chlorobenzoic acid, more preferably, for example, saturated , aliphatic monopercarboxylic acids having 2 to 4 carbon atoms such as a peracetic acid, a perpropionic acid and a perbutyric acid, most preferably a perpropionic acid which is used for the reaction with cyclohexanone in the preparation of $\epsilon$-caprolactone.

In the present invention, as a stabilizer of the percarboxylic acid, a pyridine derivative including picoline (methylpyridine) such as 2-picoline, 3-picoline and 4-picoline, ethylpyridine such as 2-ethylpyridine, 3-ethylpyridine and 4-ethylpyridine, conyrine (2-propylpyridine), lutidine (dimethylpyridine) such as 2,3-lutidine, 2,4-lutidine, 2,5-lutidine, 2,6-lutidine, 3,4-lutidine and 3,5-lutidine, 2-methyl-3-ethylpyridine and N-oxide thereof such as 2-picoline-N-oxide, 3-picoline-N-oxide, 4-picoline-N-oxide and 2,6-lutidine-N-oxide is preferably employed singly or in combination, and it is a characteristic of the present invention to employ 2-picoline, 2,6-lutidine or N-oxide thereof.

The process of the present invention is employed suitably as a process for stabilizing a solution of a percarboxylic acid in which the percarboxylic acid as described above is dissolved in an inert solvent which is, for example, carboxylic acids such as formic acid, acetic acid, propionic acid, butyric acid, isobutyric acid and heptanoic acid, esters such as methyl, ethyl, propyl, isopropyl, n-butyl, isobutyl, sec-butyl, tert-butyl, amyl, isoamyl, sec-amyl and tert-amyl esters of these carboxylic acids, chlorinated hydrocarbons such as chloroform, carbon tetrachloride, methylene chloride, 1,2-dichloroethane, dichloropropane, trichloroethane and tetrachloroethane, hydrocarbons such as cyclohexane, methylcyclohexane, benzene, toluene and xylene, ethers such as acetone, dioxane, diethyl ether, diisopropyl ether and dibutyl ether, water, hydrogen peroxide or a mixture thereof, but a percarboxylic acid having high purity and substantially not containing such a solvent can be also stabilized according to the process of the present invention.

A concentration of the percarboxylic acid in a solution of the percarboxylic acid as described above is about 1 to 90% by weight, preferably about 5 to 70% by weight, particularly preferably about 10 to 50% by weight.

The process of the present invention can be performed favorably by adding the stabilizer as described above to a mixture comprising hydrogen peroxide and a carboxylic acid in preparation of the percarboxylic acid from hydrogen peroxide and the carboxylic acid. However, an embodiment of the process of the present invention is not limited thereto, and may include any process as long as a state in which the stabilizer as described above is mixed with a percarboxylic acid in consequence can be maintained. For example, a pure substance of the stabilizer may be added as such to a solution of the percarboxylic acid as described above, or the stabilizer may be previously dissolved in a suitable solvent (preferably the same solvent which is used in preparation of the solution of the percarboxylic acid as described above) and then added to the solution of the percarboxylic acid as described above. Alternatively, in preparation of a solution of the percarboxylic acid as described above, a pure product of the stabilizer as described above or a solution dissolved in a solvent obtained as described above may be added to the percarboxylic acid or the solution thereof as described above.

An amount of the stabilizer as described above to be added is not specifically limited, but may be about 0.0005 to 5.0%, preferably about 0.05 to 1.0%, particularly preferably 0.1 to 0.5% based on the weight of the percarboxylic acid as described above.

The process of the present invention is effective when the stabilizer as described above exists in a solution of the percarboxylic acid as described above at a temperature range of from about $-50°$ to $150°$ C., preferably from about $-10°$ to $100°$ C., particularly preferably from a room temperature ($20°$ to $30°$ C.) to $80°$ C. and under either of normal pressure, low pressure or high pressure.

The process of the present invention can be applied, as described above, to stabilization of a percarboxylic acid which is used for chemical reactions such as epoxidation, hydroxylation, lactonization, formation of quinone, aromatic ring opening, formation of phenol and oxidation of ketone, and the process of the present invention can be applied suitably to a manufacturing process in which a percarboxylic acid is required to exist stably over a long term, particularly, in "a process for preparing $\epsilon$-caprolactone in which $\epsilon$-caprolactone is prepared by oxidizing cyclohexanone by a solution containing a perpropionic acid, wherein an excess amount of the perpropionic acid to cyclohexanone is used to allow said oxidation reaction to occur, and the excess amount of the perpropionic acid is separated from an oxidation reaction mixture by evaporation to be used repeatedly", as disclosed in Japanese Unexamined Patent Publication No. 124781/1983.

EXAMPLES

In the following, the present invention is described in detail by referring to Examples and Comparative examples. The process of the present invention is not limited by Examples as described below as long as it is within the scope of the present invention.

In each of Examples and Comparative examples, a concentration of a perpropionic acid in a reaction mixture was measured according to "the iodine titration method".

Further, in each of Examples and Comparative examples, abbreviations and a deterioration rate R (%) of a perpropionic acid are defined as follows.

(PPA)$_0$: Concentration of a perpropionic acid in a reaction mixture when a test of stability with lapse of time is started (% by weight)

(PPA)$_t$: Concentration of a perpropionic acid in a reaction mixture t hours after starting of a test of stability with lapse of time (% by weight)

$$R\ (\%) = \frac{(PPA)_0 - (PPA)_t}{(PPA)_0} \times 100$$

EXAMPLE 1

Preparation of Perpropionic Acid Solution

A crude solution of a perpropionic acid was prepared by using an experimental apparatus of which a summarized flow chart is shown in FIG. 1.

Specifically, into a glass reactor 1 having a volume of 2 equipped with a distillation column 2 with 20 sheets of Oldershaw plates and a reflux condenser 3 equipped with a settler, a solution 5 comprising 504 g of a propionic acid, 126 g of 1,2-dichloroethane and 1,6 g of an orthoboric acid with 0.09 g of 2-picoline as a stabilizer were charged in a total amount of 631.69 g.

Next, the reactor 1 was immersed in an oil bath and heated to $100°$ to $110°$ C. whereby the solution 5 was heated up to a boiling point while refluxing under a reduced pressure of 100 torr, and 60% by weight of a hydrogen peroxide aqueous solution 6 was added over 30 minutes in a total amount of 26.85 g. At the same time, from the top of the distillation column 2, a distilled water 7 was added over 2.5 hours at a rate of 5.3 g/hour. A temperature in the reactor 1 was $65°$ C., and an organic phase 8 in which hetero azeotropic substances were condensed was recirculated from the reflux condenser 3 equipped with a settler to maintain generation of reflux. On the other hand, an aqueous phase 9 condensed was decanted and removed successively from the reflux condenser 3 equipped with a settler.

After a reaction of a propionic acid and hydrogen peroxide was continued for 3 hours as described above, heating of the reactor 1 was stopped to terminate the reaction.

Precipitates of a boric acid in a reaction mixture taken out from the reactor 1 were filtered off through a glass filter 4 to obtain 641 g of a crude solution 10 (reaction mixture) of a perpropionic acid.

A conversion based on the charged hydrogen peroxide, an yield of the perpropionic acid and a concentration of the perpropionic acid in the reaction mixture (a concentration of the perpropionic acid immediately after synthesis) are shown in Table 1.

An amount of 2-picoline added was found to be 0.24% relative to the weight of the perpropionic acid formed.

2-Picoline-N-oxide was found to be produced in the reaction mixture.

Stability Test of Reaction Mixture with Lapse of Time

Into a glass vessel having an inner volume of 100 ml equipped with a reflux concenser, a sampling aperture and a thermometer, 50 g of the above reaction mixture was charged from the sampling aperture, and the sampling aperture was immediately closed tightly. Subsequently, the vessel was immersed in an oil bath, and a temperature of the reaction mixture was elevated to 65° C., followed by maintenance of this state for 12 hours. Meanwhile, a gas generated by decomposition of the perpropionic acid in the reaction mixture was discharged in the air through the reflux condenser.

When a temperature of the reaction mixture was reached to 65° C. by heating the vessel in an oil bath, the sampling aperture was opened, and a predetermined amount of the reaction mixture was taken out by means of a pipette. A concentration of the perpropionic acid in the reaction mixture was measured, and the value obtained was defined as a value of 0 hour after synthesis of the perpropionic acid. Immediately after a predetermined amount of the reaction mixture was taken out by means of a pipette, the sampling aperture was closed tightly.

Thereafter, the above procedures were repeated every two hours, and a concentration of the perpropionic acid in the reaction mixture was measured to determine a deterioration rate of the perpropionic acid. The results are shown in Table 1.

EXAMPLE 2

Preparation of Perpropionic Acid Solution

The procedures were carried out in the same manner as in Example 1 except for charging into the reactor 1 a solution 5 comprising 0.10 g of 2,6-lutidine in place of 2-picoline as a stabilizer and the same amounts of a propionic acid, 1,2-dichloroethane and an orthoboric acid as in Example 1 in a total amount of 631.7 g, to prepare 639 g of a crude solution 10 (reaction mixture) of a perpropionic acid.

A conversion based on the charged hydrogen peroxide, an yield of the perpropionic acid and a concentration of the perpropionic acid in the reaction mixture (a concentration of the perpropionic acid immediately after synthesis) are shown in Table 1.

An amount of 2,6-lutidine added was found to be 0.27% relative to the weight of the perpropionic acid formed.

2,6-Lutidine-N-oxide was found to be produced in the reaction mixture.

Stability Test of Reaction Mixture with Lapse of Time

According to the same manner as in Example 1, a stability test of the reaction mixture with a lapse of time was conducted. The results are shown in Table 1.

EXAMPLE 3

Preparation of Perpropionic Acid Solution

The procedures were carried out in the same manner as in Example 1 except for charging into the reactor 1 a solution 5 comprising 504 g of a propionic acid, 126 g of 1,2-dichloroethane and 6.4 g of an orthoboric acid with 0.36 g of 2-picoline as a stabilizer in a total amount of 636.76 g, adding 60% by weight of a hydrogen peroxide aqueous solution 6 in a total amount of 107.4 g to the solution 5 and at the same time adding the distilled water 7 from the top of the distillation column 2 over 2.5 hours at a rate of 21 to 22 g/hour, to prepare 671 g of a crude solution 10 (reaction mixture) of a perpropionic acid.

A conversion based on the charged hydrogen peroxide, an yield of the perpropionic acid and a concentration of the perpropionic acid in the reaction mixture (a concentration of the perpropionic acid immediately after synthesis) are shown in Table 1.

An amount of 2-picoline added was found to be 0.24% relative to the weight of the perpropionic acid formed.

2-Picoline-N-oxide was found to be produced in the reaction mixture.

Stability Test of Reaction Mixture with Lapse of Time

According to the same manner as in Example 1, a stability test of the reaction mixture with a lapse of time was conducted. The results are shown in Table 1.

EXAMPLE 4

Preparation of Perpropionic Acid Solution

The procedures were carried out in the same manner as in Example 3 except for charging into the reactor 1 a solution 5 comprising 0.41 g of 2,6-lutidine in place of 2-picoline as a stabilizer and the same amounts of a propionic acid, 1,2-dichloroethane and an orthoboric acid as in Example 3 in a total amount of 636.81 g, to prepare 660 g of a crude solution 10 (reaction mixture) of a perpropionic acid.

A conversion based on the charged hydrogen peroxide, an yield of the perpropionic acid and a concentration of the perpropionic acid in the reaction mixture (a concentration of the perpropionic acid immediately after synthesis) are shown in Table 1.

An amount of 2,6-lutidine added was found to be 0.27% relative to the weight of the perpropionic acid formed.

2,6-Lutidine-N-oxide was found to be produced in the reaction mixture.

Stability Test of Reaction Mixture with Lapse of Time

According to the same manner as in Example 1, a stability test of the reaction mixture with a lapse of time was conducted. The results are shown in Table 1.

Comparative Examples 1 to 4

Preparation of Perpropionic Acid Solution

The procedures were carried out in the same manner as in Example 3 except for charging into the reactor 1 a solution 5 comprising the same amounts of a propionic acid, 1,2-dichloroethane and an orthoboric acid as in Example 3 and, 0.64 of a dipicolinic acid in Comparative example 1, 0.32 g of a dipicolinic acid in Comparative example 2, 1.02 g of tributyl phosphate in Comparative example 3 and 0.47 g of a picolinic acid in place of 2-picoline as a stabilizer, respectively, in a total amount of 637.04 g in Comparative example 1, 636.72 g in Comparative example 2, 637.42 g in Comparative example 3 and 636.87 g in Comparative example 4, respectively, to prepare crude solutions 10 (reaction mixtures) of a perpropionic acids in an amount of 671 g in Comparative example 1, 668 g in Comparative example 2, 672 g in Comparative example 3 and 666 g in Comparative example 4, respectively.

Conversions based on the charged hydrogen peroxide, yields of the perpropionic acids and concentrations of the perpropionic acids in the reaction mixtures (concentrations of the perpropionic acids immediately after synthesis) are shown in Table 1.

Amounts of the stabilizers added in Comparative examples 1 to 4 relative to the weights of the perpropionic acids formed are shown below.

| Comparative example No. | Name of stabilizer | Amount added (%) |
|---|---|---|
| 1 | Dipicolinic acid | 0.42 |
| 2 | Dipicolinic acid | 0.22 |
| 3 | Tributyl phosphate | 0.69 |
| 4 | Picolinic acid | 0.32 |

Stability Test of Reaction Mixture with Lapse of Time

According to the same manner as in Example 1, stability tests of the reaction mixtures obtained in Comparative example 1, Comparative example 2, Comparative example 3 and Comparative example 4 with a lapse of time were conducted. The results are shown in Table 1.

TABLE 1

| Item | | Example No. | | | | Comparative example No. | | | |
|---|---|---|---|---|---|---|---|---|---|
| | | 1 | 2 | 3 | 4 | 1 | 2 | 3 | 4 |
| Name of stabilizer | | 2-Picoline | 2,6-Lutidine | 2-Picoline | 2,6-Lutidine | Dipicolinic acid | Dipicolinic acid | Tributyl phosphate | picolinic acid |
| Amount of stabilizer added (%) | | 0.09 | 0.10 | 0.36 | 0.41 | 0.64 | 0.32 | 1.02 | 0.47 |
| $H_2O_2$ conversion (%) | | 92.3 | 92.2 | 95.3 | 94.6 | 95.0 | 91.3 | 95.2 | 94.4 |
| Yield of perpropionic acid (%) | | 86.7 | 87.4 | 86.2 | 87.5 | 88.6 | 84.6 | 87.2 | 85.9 |
| Concentration of perpropionic acid immediately after synthesis (% by weight) | | 5.73 | 5.81 | 22.1 | 22.8 | 22.9 | 21.8 | 22.3 | 22.1 |
| Change of concentration of perpropionic acid and deterioration rate with lapse of time (temperature: 65° C.) | | | | | | | | | |
| Concentration (% by weight) | 0 hour | 5.70 | 5.81 | 21.6 | 22.7 | 22.9 | 21.8 | 22.0 | 22.5 |
| | 2 hours | 5.70 | 5.81 | 22.1 | 22.3 | 22.2 | 21.6 | 21.7 | 21.8 |
| | 4 hours | 5.64 | 5.65 | 21.5 | 21.5 | 21.7 | 20.5 | 21.1 | 20.6 |
| | 6 hours | 5.66 | 5.56 | 20.9 | 20.7 | 20.1 | 19.7 | 20.8 | 19.4 |
| | 8 hours | 5.62 | 5.55 | 19.6 | 19.6 | 19.3 | 17.6 | 19.5 | 17.6 |
| | 10 hours | 5.37 | 5.07 | 18.8 | 19.3 | 18.2 | 17.0 | 18.9 | 16.6 |
| | 12 hours | 5.56 | 5.13 | 18.3 | 18.7 | 17.5 | 15.7 | 17.6 | 15.7 |
| Deterioration rate (%) | 0 hour | — | — | — | — | — | — | — | — |
| | 2 hours | 0.0 | 0.0 | — | 1.8 | 3.1 | 0.9 | 1.4 | 3.1 |
| | 4 hours | 1.1 | 2.7 | 0.5 | 5.3 | 5.2 | 6.0 | 4.1 | 8.4 |
| | 6 hours | 0.7 | 4.3 | 3.2 | 8.8 | 12.2 | 9.6 | 5.5 | 13.8 |
| | 8 hours | 1.4 | 4.5 | 9.3 | 13.7 | 15.7 | 19.3 | 11.4 | 21.8 |
| | 10 hours | 5.8 | 12.7 | 13.0 | 15.0 | 20.5 | 22.0 | 14.1 | 26.2 |
| | 12 hours | 2.5 | 11.7 | 15.3 | 17.6 | 23.6 | 28.0 | 20.0 | 30.2 |

Remarks: Yield of the perpropionic acid is indicated as a value based on the supplied hydrogen peroxide.

As described above, the stabilizers known in the art such as a picolinic acid, a dipicolinic acid and tributyl phosphate had the drawback that they cannot be said to be satisfactory in the points of a stabilizing effect on a solution of a percarboxylic acid and economy. However, according to the present invention, by using at least one pyridine derivative such as picoline, ethylpyridine, conyrine, lutidine and N-oxide thereof, particularly 2-picoline, 2,6-lutidine and N-oxide thereof as a stabilizer, a process for stabilizing a percarboxylic acid, which can be applied industrially, can be provided by employing such novel stabilizer which is more excellent in a stabilizing effect on a solution of a percarboxylic acid over a long term than the stabilizers known in the art, inexpensive and commercially available.

We claim:

1. A process for stabilizing a percarboxylic acid characterized in that the percarboxylic acid is mixed with at least one pyridine derivative selected from the group consisting of picoline, ethylpyridine, conyrine, lutidine and N-oxide thereof.

2. The process according to claim 1, wherein said pyridine derivative is selected from the group consisting of 2-picoline, 3-picoline, 4-picoline, 2-ethylpyridine, 3-ethylpyridine, 4-ethylpyridine, conyrine, 2,3-lutidine, 2,4-lutidine, 2,5-lutidine, 2,6-lutidine, 3,4-lutidine, 3,5-lutidine, 2-methyl-3-ethylpyridine, 2-picoline-N-oxide, 3-picoline-N-oxide, 4-picoline-N-oxide and 2,6-lutidine-N-oxide.

3. The process according to claim 2, wherein said pyridine derivative is 2-picoline or 2,6-lutidine or N-oxide thereof.

4. The process according to claim 1, wherein an amount of the pyridine derivative is 0.0005 to 5.0% based on the weight of the percarboxylic acid.

5. The process according to claim 4, wherein an amount of the pyridine derivative is 0.05 to 1.0% based on the weight of the percarboxylic acid.

6. The process according to claim 5, wherein an amount of the pyridine derivative is 0.1 to 0.5% based on the weight of the percarboxylic acid.

7. The process according to claim 1, wherein the percarboxylic acid is selected from the group consisting of saturated aliphatic monopercarboxylic acids having 1 to 7 carbon atoms, unsaturated aliphatic monopercarboxylic acids having 3 to 4 carbon atoms, alicyclic monopercarboxylic acids and aromatic monopercarboxylic acids.

8. The process according to claim 7, wherein the percarboxylic acid is selected from the group consisting of a performic acid, a peracetic acid, a perpropionic acid, a perbutyric acid, a perisobutyric acid, a perheptoic acid, a percrotonic acid, a perisocrotonic acid, a peracrylic acid, a permethacrylic acid, a percyclohexanoic acid, a perbenzoic acid, a pertoluic acid, a monoperphthalic acid and a per-m-chlorobenzoic acid.

9. The process according to claim 7, wherein the percarboxylic acid is selected from the group consisting of saturated aliphatic monopercarboxylic acids having 2 to 4 carbon atoms.

10. The process according to claim 8, wherein the percarboxylic acid is a peracetic acid, a perpropionic acid or a perbutyric acid.

11. The process according to claim 10, wherein the percarboxylic acid is a perpropionic acid.

12. The process according to claim 1, wherein the percarboxylic acid is a pure product or a solution dissolved in a solvent.

13. The process according to claim 12, wherein a concentration of the solution of the percarboxylic acid is 1 to 90% by weight.

14. The process according to claim 13, wherein a concentration of the solution of the percarboxylic acid is 5 to 70% by weight.

15. The process according to claim 14, wherein a concentration of the solution of the percarboxylic acid is 10 to 50% by weight.

* * * * *